US011701174B2

(12) United States Patent
Harrah et al.

(10) Patent No.: US 11,701,174 B2
(45) Date of Patent: Jul. 18, 2023

(54) MEDICAL DEVICE HAVING A PLURALITY OF LUMENS AND A PORT

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Arpita Banerjee, Bangalore (IN); Sandesh Gavade, Bangalore (IN); Abhijit Takale, Pune (IN); Pavan Misra, Bangalore (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 961 days.

(21) Appl. No.: 15/416,766

(22) Filed: Jan. 26, 2017

(65) Prior Publication Data

US 2017/0215964 A1   Aug. 3, 2017

Related U.S. Application Data

(60) Provisional application No. 62/288,780, filed on Jan. 29, 2016.

(51) Int. Cl.
*A61B 18/24* (2006.01)
*A61B 17/22* (2006.01)
(Continued)

(52) U.S. Cl.
CPC ............ *A61B 18/245* (2013.01); *A61B 1/018* (2013.01); *A61B 1/0125* (2013.01); *A61B 1/05* (2013.01);
(Continued)

(58) Field of Classification Search
USPC ......................................... 600/108, 123, 156
See application file for complete search history.

(56) References Cited

U.S. PATENT DOCUMENTS 4,842,579 A * 6/1989 Shiber .................. A61B 18/082
   606/159
5,083,549 A * 1/1992 Cho .................... A61B 1/00071
   600/108
(Continued)

FOREIGN PATENT DOCUMENTS

WO   WO 03/030981 A1   4/2003

OTHER PUBLICATIONS

International Search Report and Written Opinion for International Application No. PCT/US2017/015119, dated May 4, 2017 (12 pages).

*Primary Examiner* — John P Leubecker
(74) *Attorney, Agent, or Firm* — Bookoff McAndrews, PLLC

(57) ABSTRACT

Devices, systems, and methods are provided for breaking a kidney stone(s) into smaller particles, fragments, and/or stone dust; and removing the same from a patient. The medical device may include a tube having a distal end, a proximal end, a port located proximal of the distal end, and a length of the tube extending between the proximal end and the distal end. A first portion of the tube may be proximal of the port and have a first cross-sectional area, while a second portion of the tube may be distal of the port and have a second cross-sectional area smaller than the first cross-sectional area. A first lumen may extend from the proximal end to the distal end of the tube. A second lumen may in communication with the port to fluidly connect the proximal end of the tube with the port.

20 Claims, 4 Drawing Sheets

(51) Int. Cl.
*A61B 1/012* (2006.01)
*A61B 1/307* (2006.01)
*A61B 18/26* (2006.01)
*A61B 1/018* (2006.01)
*A61B 1/05* (2006.01)
*A61B 1/06* (2006.01)
*A61B 90/30* (2016.01)
*A61B 17/00* (2006.01)
*A61B 18/00* (2006.01)

(52) U.S. Cl.
CPC ............ *A61B 1/0676* (2013.01); *A61B 1/307* (2013.01); *A61B 17/22004* (2013.01); *A61B 18/26* (2013.01); *A61B 90/30* (2016.02); *A61B 2017/0034* (2013.01); *A61B 2017/22074* (2013.01); *A61B 2017/22079* (2013.01); *A61B 2018/00511* (2013.01); *A61B 2018/00982* (2013.01); *A61B 2218/007* (2013.01)

(56) References Cited

U.S. PATENT DOCUMENTS

| | | | |
|---|---|---|---|
| 5,224,942 A * | 7/1993 | Beuchat | A61B 18/26 606/4 |
| 5,836,909 A * | 11/1998 | Cosmescu | A61M 1/743 604/35 |
| 5,899,915 A * | 5/1999 | Saadat | A61B 17/32002 604/22 |
| 7,341,556 B2 * | 3/2008 | Shalman | A61B 1/00091 600/157 |
| 8,747,388 B2 * | 6/2014 | Pandey | A61M 25/0017 604/93.01 |
| 9,655,678 B2 * | 5/2017 | Irby, III | A61B 17/22 |
| 2001/0001059 A1 * | 5/2001 | Love | A61B 10/0045 435/7.1 |
| 2005/0090709 A1 * | 4/2005 | Okada | A61B 1/0005 600/104 |
| 2005/0107736 A1 * | 5/2005 | Landman | A61M 25/0068 604/93.01 |
| 2007/0088256 A1 | 4/2007 | Intoccia et al. | |
| 2007/0161963 A1 | 7/2007 | Smalling | |
| 2008/0188866 A1 | 8/2008 | Karpiel et al. | |
| 2008/0262308 A1 * | 10/2008 | Prestezog | A61B 1/307 600/123 |
| 2013/0165944 A1 | 6/2013 | Gal et al. | |
| 2014/0275762 A1 * | 9/2014 | Irby, III | A61B 17/22 600/103 |
| 2015/0196361 A1 | 7/2015 | Preiss et al. | |
| 2015/0335813 A1 * | 11/2015 | Qian | A61M 3/022 604/35 |
| 2016/0166320 A1 * | 6/2016 | Ciulla | A61B 18/26 606/14 |
| 2017/0007277 A1 * | 1/2017 | Drapeau | A61B 17/320016 |
| 2017/0215965 A1 * | 8/2017 | Harrah | A61B 1/0684 |

* cited by examiner

MEDICAL DEVICE HAVING A PLURALITY OF LUMENS AND A PORT

CROSS-REFERENCE TO RELATED APPLICATIONS

This patent application claims the benefit of priority under 35 U.S.C. § 119 to U.S. Provisional Patent Application No. 62/288,780, filed Jan. 29, 2016, which is herein incorporated by reference in its entirety.

TECHNICAL FIELD

The present disclosure relates generally to medical devices. More particularly, the disclosure relates to medical devices used, for example, in breaking objects into smaller particles, and removing the resulting particles from a patient. The disclosure also relates to methods of using such devices.

BACKGROUND OF THE DISCLOSURE

The incidence of hospitalization for the removal of urinary calculi, commonly referred to as kidney stones, has been estimated at 200,000 cases per year. A vast majority of these patients pass their stones spontaneously; however, in the remainder, the kidney stone(s) become impacted in the ureter, a muscle tube joining the kidney to the bladder. An impacted kidney stone is a source of intense pain and bleeding, a source of infection and, if a stone completely blocks the flow of urine for any extended length of time, can cause the loss of a kidney.

Various methods have been utilized to break the stone into smaller fragments. One such method is stone dusting. Stone dusting is used by some urologists to fragment and evacuate stones from a kidney and is often performed by a Ureteroscope. Intense light energy from a laser within the Ureteroscope breaks the stone into increasingly smaller pieces. Rather than breaking up the stone into chunks, which are removed by baskets, dusting generates very small fragments that are capable of being passed naturally. However, in some cases, these small stone fragments may not pass naturally. In theory, any of these small stone fragments that do not evacuate through natural urine flow, could be a seed for new stone growth. Thus, the application of suction may be employed to remove the stone dust. Providing suction requires a lumen with sufficient internal cross-sectional area to allow stone fragments and/or dust to pass through without clogging. Adding such a lumen to a traditional ureteroscope may increase the ureteroscope's cross-section to a size that is no longer capable of reaching the target kidney stone. For example, the kidney stone may be within the kidney, or, specifically, within a calyx of the kidney. Often, the space within the kidney and/or a calyx of the kidney is more limited than the space within the ureter and is not large enough to accommodate a ureteroscope with the added width of a suction lumen. The disclosure addresses the above-mentioned process and other problems in the art.

SUMMARY OF THE DISCLOSURE

Aspects of the present disclosure provide methods for breaking an object into smaller particles and removing said particles from portions of the human body with limited space.

It is to be understood that both the foregoing general description and the following detailed description are exemplary and explanatory only and are not restrictive.

In one example, a medical device may include a tube having a distal end, a proximal end, a port located proximal of the distal end, and a length of the tube extending between the proximal end and the distal end, wherein a first portion of the tube may be proximal of the port and may have a first cross-sectional area and a second portion of the tube may be distal of the port and may have a second cross-sectional area smaller than the first cross-sectional area; a first lumen may extend from the proximal end to the distal end of the tube, and a second lumen may be in communication with the port and may be fluidly connecting the proximal end of the tube with the port.

Examples of the medical device may additionally and/or alternatively include one or more other features. Features of the various examples described in the following may be combined unless explicitly stated to the contrary. For example, the port may be distal to the proximal end by a distance of approximately half to approximately three-quarters the length of the tube. A laser fiber may be disposed within the first lumen. A fluid supply assembly may be connected to the first lumen. The first lumen may be configured to simultaneously connect to a fluid supply apparatus and a laser control. A laser may extend from the laser control into the first lumen and to the distal end. A vacuum source may be connected to the second lumen. The port may be angled relative to a longitudinal axis of the second lumen. An illumination device may extend through the tube. An imaging device may extend through the tube. The first cross-sectional area may be approximately 3 mm to approximately 8 mm. The second cross-sectional area may be approximately 2 mm to approximately 5 mm. The port may be substantially crescent-shaped. The port may be located approximately 5 cm to approximately 15 cm from the distal end. The second lumen may terminate at the port.

In another example, a method of operating a medical device may include positioning a distal end of a medical device at a target area, the medical device including a first lumen and a second lumen, wherein the second lumen is in fluid communication with a port and the port is proximal of the distal end of the medical device, supplying fluid through the first lumen, and applying suction through the second lumen.

Examples of the method of operating the medical device may additionally and/or alternatively include one or more other features. For example, the port may be at least 10 cm from the distal end of the medical device. The target area may be within a patient's kidney and the port is positioned within the patient's ureter.

In another example, a medical device may include a tube having a distal end, a proximal end, and a port located at least approximately 10 cm from the distal end, a first lumen in communication with the distal end and fluidly connecting the distal end with a fluid supply assembly, and a second lumen in communication with the port and fluidly connecting a vacuum source with the port.

Examples of the medical device may additionally and/or alternatively include one or more other features. Features of the various examples described in the following may be combined unless explicitly stated to the contrary. For example, the port may be at least partially distal-facing.

BRIEF DESCRIPTION OF THE DRAWINGS

The accompanying drawings, which are incorporated in and constitute a part of this specification, illustrate various examples and together with the description, serve to explain the principles of the disclosure.

DETAILED DESCRIPTION

Reference is now made in detail to examples of the present disclosure, examples of which are illustrated in the accompanying drawings. Wherever possible, the same reference numbers will be used throughout the drawings to refer to the same or like parts. The term "distal" refers to a position farther away from a user end of the device. The term "proximal" refers a position closer to the user end of the device. As used herein, the terms "approximately" and "substantially" indicate a range of values within +/−5% of a stated value.

Overview

Aspects of the present disclosure relate to systems and methods for breaking kidney stones into smaller particles and removing those particles from a target area of a patient's body without adding to the cross-sectional width of the portion of the device entering the target area. The medical device described herein may work by positioning within the target area a distal end of a ureteroscope, while positioning a suction port of a suction lumen in a cavity and/or lumen of the body having greater space and located proximal of the target area. For example, a distal end of a ureteroscope may be positioned within the kidney, or more specifically, a calyx of the kidney, and the suction port may be positioned within the ureter which is proximal to and, often, has more space than the kidney and/or calyx. A laser, disposed within a lumen of the ureteroscope and thus positioned within the target area, may be used to break up kidney stones into particles. During and/or after the laser process, the suction port, positioned proximally of the target area, may vacuum the resulting particles from the body.

Though several examples herein describe the distal end of the medical device within the kidney and the suction port within the ureter, the present disclosure should not be limited thereto. For example, while the distal end of the medical device is within the kidney, the suction port may be anywhere within the urinary tract that is proximal to the distal end of the medical device, including more proximal portions of the kidney, the bladder and/or the urethra. Additionally, the target area may be any location. In some examples, the target area may be anywhere within a urinary tract. The target area may be a site in the body where a kidney stone is known or suspected to be located. For example, if a kidney stone is detected within the ureter, the ureter (or portion thereof) may be the target area and the suction port may be positioned anywhere proximally of the target area, including but not limited to, more proximal portions of the ureter, the bladder, and/or the urethra.

Detailed Examples

Figure 1:
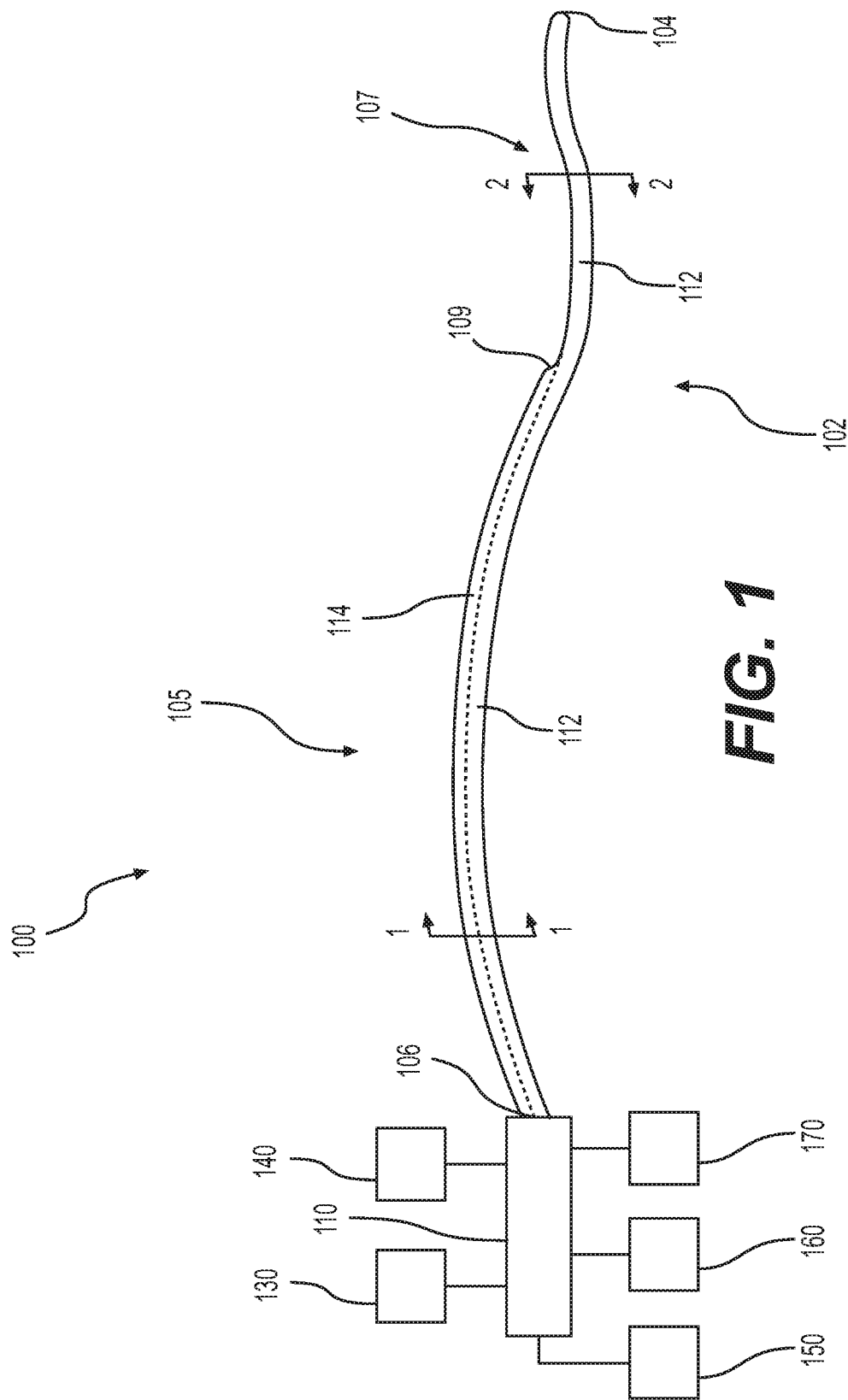
FIG. 1 illustrates an exemplary medical device, including a tube, a handle portion, a fluid supply assembly, a laser source, an illumination source, an imaging apparatus, and a vacuum source.

FIG. 1 illustrates an exemplary medical device 100 for removing stone fragments/dust while minimizing the diameter of the portion of the device that is disposed within the target area, e.g., the kidney. The device 100 may include a tube 102. Tube 102 may be a hollow, flexible, elongate tube having a suction port 109, a proximal end 106, and a distal end 104. Tube 102 may further include having independent first and second lumens 112 and 114. Proximal end 106 of tube 102 may be coupled to a handle portion 110. The handle portion 110 and/or the proximal end 106 of tube 102 may be attached to a laser control 130, a fluid supply assembly 140, a vacuum source 150, an illumination source 160, and/or an imaging apparatus 170.

A. The Handle Portion

Handle portion 110 can be attached to tube 102 by, for example, welding, a locking configuration, adhesive, or integrally formed with tube 102. The handle portion 110 may include a plurality of ports. For example, a first port may place first lumen 112 of tube 102 in fluid communication with fluid supply assembly 140 and a second port may place second lumen 114 of tube 102 in fluid communication vacuum source 150. Additional ports and lumens may be provided for supplying to distal end 104 of tube 102 and/or a laser fiber coupled to laser control 130, illumination device coupled to illumination source 160, and/or an imaging device coupled to the imaging apparatus 170. For example, first lumen 112 may include two ports, a first for connecting the fluid supply assembly 140 and a second for connecting laser fiber 120 and/or laser source 130. The handle portion 110 may include an actuating mechanism (not shown) to actuate one or more medical devices that may be located at the distal end 104 of tube 102. For example, the handle portion may include an actuating mechanism to power on or off the laser, the illumination device, and/or the imaging device.

The fluid supply assembly 140 may be any device and/or devices that can supply fluid (e.g., saline) to first lumen 112. The fluid supply assembly 140 may include, but is not limited to, a fluid source, a pump, a control system, a heat exchanger, a filter, a temperature sensor, a pressure sensor, a supply line, and/or various user input devices.

The vacuum source may be any device and/or devices that can provide suction to lumen 114 (e.g., house vacuum, vacuum pump, etc.). The vacuum source 150 may provide suction and allow the operator to vary the suction. The vacuum source 150 may be located near the patient or may be located remotely (such as a vacuum source located on a wall). In some examples, vacuum source 150 may be included in a single unit with fluid supply assembly 140. For example, fluid supply assembly 140 and vacuum source 150 may be the inlet and outlet, respectively, of a peristaltic pump.

B. The Tube

As noted above, tube 102 may further include two independent lumens, first lumen 112 and second lumen 114. While two lumens are illustrated in FIG. 1, tube 102 may include any number of lumens. The lumens included in tube 102 may be any size, shape, and/or in any configuration. Exemplary cross-sections of tube 102 at two positions along its length, including first lumen 112 and/or second lumen 114 will be described in further detail below with respect to FIGS. 2 and 3.

First lumen 112 and/or second lumen 114 may include any suitable coating. For example, first lumen 112 and/or second lumen 114 may include a layer of lubricous material, for example, to facilitate insertion of any instrument and/or device or prevent clogging of stone fragments/dust. First lumen 112 and/or second lumen 114 may be defined by elongate hollow lumens that extend within tube 102.

Figure 5:
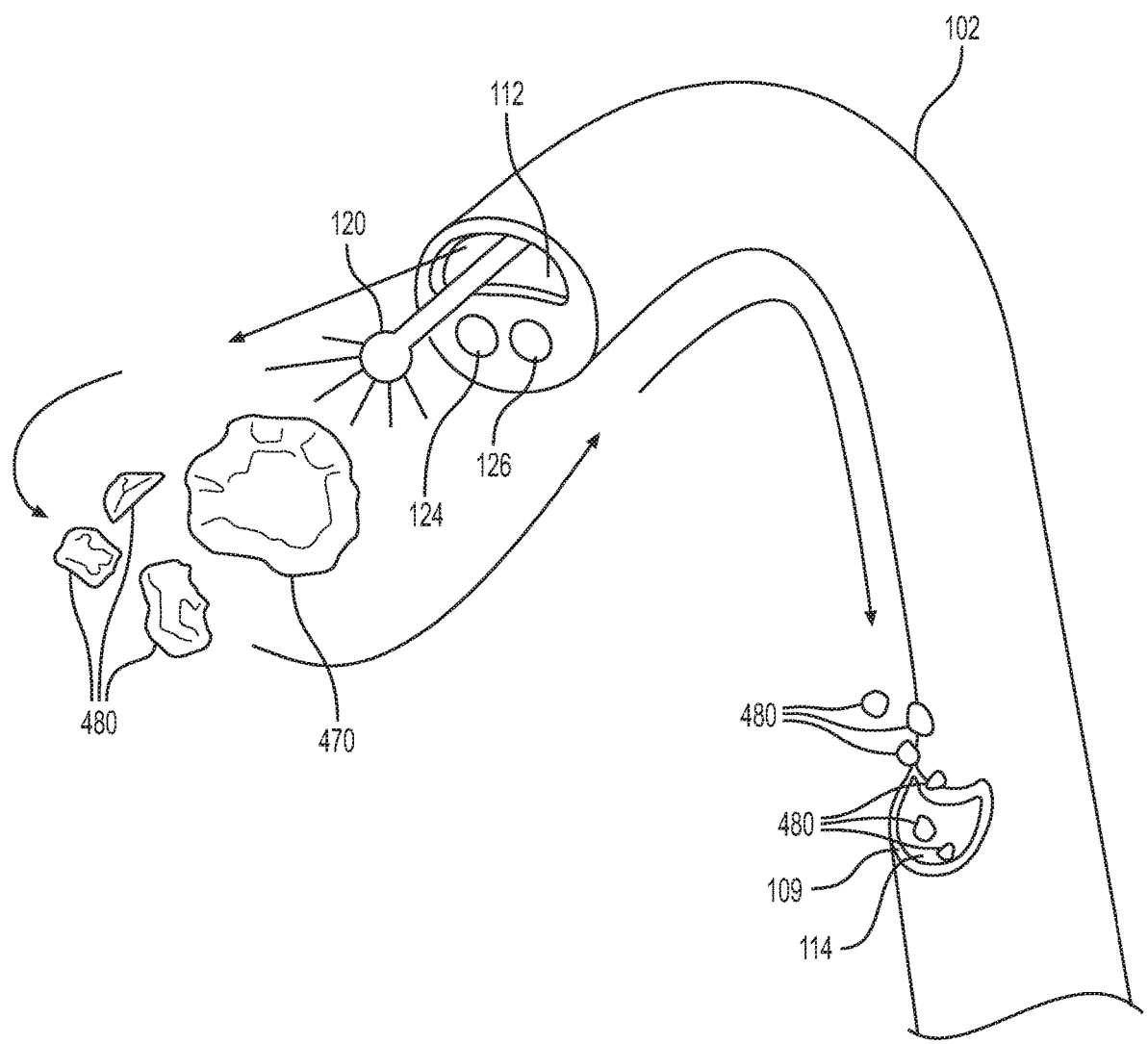
FIG. 5 illustrates an exemplary operation of the medical device of FIG. 1.

First lumen 112 may extend between proximal end 106 and distal 104. First lumen 112 may be open (e.g., open to a body cavity like a kidney) at the distal end 104 of tube 102 to allow introduction of a laser fiber 120 and/or flow of irrigation fluid. The distal opening of first lumen 112 may be substantially perpendicular to the tube (e.g., as shown in FIG. 5), may be tapered or angled, or may be in any other suitable shape, size, and/or orientation. The proximal end of first lumen 112 may have any shape or configuration. For example, first lumen 112 may have two openings or may fork at or near the proximal end 106 of tube 102. First lumen 112 may be configured in any way that would allow for first lumen 112 to be simultaneously connected to fluid supply apparatus 140 and laser control 130. This may allow laser fiber 120 to be disposed within first lumen 112 at the same time fluid is introduced through first lumen 112.

Second lumen 114 may extend between proximal end 106 and suction port 109. Second lumen 114 may be in fluid communication with vacuum source 150 and suction port 109. Suction port 109 may be open (e.g., open to a body cavity like a ureter) to allow the application of suction through second lumen 114. Suction port 109 may be distal of proximal end 106 by a distance no greater than between approximately half and approximately three-fourths of the length of tube 102 (e.g., from proximal end 106 to distal end 104), or no greater than approximately two-thirds of the length of tube 102. In some examples, suction port 109 may be no less than between approximately 3 cm to approximately 15 cm from distal end 104, or no less than approximately 10 cm from distal end 104. Portions of tube 102 proximal to suction port 109 (e.g., first portion 105) of tube 102 may include both second lumen 114 and first lumen 112. Portions of tube 102 distal of suction port 109 (e.g., second portion 107) may include first lumen 112, but not include second lumen 114. As such, the cross-sectional area of first portion 105 of tube 102 may be larger than the cross-sectional area of second portion 107 of tube 102. For example, the cross-sectional area of first portion 105 of tube 102 may be approximately 3 mm to approximately 8 mm, approximately 4 to approximately 7 mm, or approximately 4 mm to approximately 6 mm and the cross-sectional area of second portion 107 of tube 102 may be approximately 2 mm to approximately 5 mm, approximately 2.5 mm to approximately 4.5 mm, or approximately 3 mm to approximately 4 mm.

In some examples, suction port 109 may be substantially or at least partially distal-facing. In some examples, suction port 109 may be angled relative to the longitudinal axis of second lumen 114. For example, at suction port 109, a wall of second lumen 114 that is opposite first lumen 112 may terminate proximal to a wall of second lumen 114 that is adjacent to first lumen 112. The walls connecting the two may form an accurate angle with longitudinal axis of the second lumen 114 between approximately 10 degrees and approximately 80 degrees, approximately 30 degrees and approximately 60 degrees, or approximately 45 degrees. The cross-sectional shape of suction port 109 may be any shape, including but not limited to a shape corresponding to the cross-sectional shape of second lumen 114 (as described further below with respect to FIG. 2). For example, as shown in FIG. 5, suction port 109 may be substantially crescent-shaped.

Tube 102 may be circular, ovoidal, irregular, and/or any shape suitable to enter a body. Further, first portion 105 of tube 102 may have the same shape or a different shape than second portion 107 of tube 102. For example, both first portion 105 and second portion 107 of tube 102 may be substantially circular or second portion 107 of tube 102 may be substantially circular while first portion 105 of tube 102 may be substantiality ovoidal or irregular (e.g., to accommodate second lumen 114). Tube 102 may have a uniform shape from proximal end 106 to distal end 104. Additionally or alternatively, first portion 105 of tube 102 may have a uniform shape from proximal end 106 to suction port 109 and/or second portion 107 of tube 102 may have a uniform shape from suction port 109 to distal end 104. In some examples, tube 102 (and/or first portion 105 or second portion 107) may having a varying shape, such as a taper at the distal end to facilitate insertion within the body.

Depending upon the particular implementation and intended use, the length of tube 102 may vary. Similarly, depending upon the particular implementation and intended use, tube 102 can be rigid along its entire length, flexible along a portion of its length, or configured for flexure at only certain specified locations. In one example, tube 102 may be flexible, adapted for flexible steering within bodily lumens, as understood in the art. For example, tube 102 can include a steering system (not shown) to move at least a portion (e.g., distal end 104) up/down and/or side-to-side. Additional degrees of freedom, provided for example via rotation, translational movement of tube 102, or additional articulation of bending sections, may also be implemented. Examples of such steering systems may include at least one of or all of pulleys, control wires, gearing, and electrical actuators.

Tube 102 may be formed of any suitable material having sufficient flexibility to traverse body cavities and tracts. In general, tube 102 may be made of any suitable material that is compatible with living tissue or a living system. That is, the tube 102 may be non-toxic or non-injurious, and it should not cause immunological reaction or rejection. In some examples, tube 102 may be made of polymetric elastomers, rubber tubing, and/or medically approved polyvinylchloride tubing. Polymeric elastomers may be, for example, EVA (Ethylene vinyl acetate), silicone, polyurethane, and/or C-Flex.

Further, the tube 102 may include any suitable coating and/or covering. For example, the outer surface may include a layer of lubricous material to facilitate insertion through a body lumen or surgical insertion. Further, tube 102 may be coated with a biocompatible material such as Teflon. To inhibit bacterial growth in the body cavity, tube 102 may be coated with an antibacterial coating. Further, an anti-inflammatory substance may also be applied to the outer surface of the tube 102, if required.

As shown in FIG. 5, tube 102 may be designed to impose minimum risk to the surrounding tissues while in use. To this end, one or more portions of tube 102 may include atraumatic geometrical structures, such as rounded or beveled terminal ends or faces (e.g., suction port 109 and/or distal end 104), to reduce trauma and irritation to surrounding tissues.

Distal end 104 of tube 102 may include visualization devices such as imaging device 124 and/or an illumination device 126. These devices may be connected to imaging apparatus 170 and illumination source 160, respectively. As shown below in FIG. 5, imaging device 124 and illumination device 126 may be disposed on a distal facing surface of tube 102. These devices and/or connecting wires may extend within the tube 102 (e.g., within a wall that separates first lumen 112 and second lumen 114). For example, imaging device 124 may be a digital camera and signal and/or power lines may extend through tube 102. Illumination device 126 may be an LED and/or a fiber may extend through tube 102.

In some examples, the light from illumination device 126 may be diffused in any way known in the art. In some examples, imaging device 124 and/or an illumination device 126 may attach to the distal end 104 using known coupling mechanisms. As illustrated herein, imaging device 124 and/or an illumination device 126 are separate and substantially circular, but imaging device 124 and/or an illumination device 126 are not limited thereto. For example, imaging device 124 and/or illumination device 126 may be any imaging device and/or illumination device known in the art. Imaging device 124 and/or an illumination device 126 may be integrated into a single unit and/or one or both may be non-circular in shape, e.g., imaging device 126 may be substantially rectangular in shape. Additionally or alternatively, the visualization devices may be detachably introduced into tube 102 through lumens, including first lumen 112 and/or second lumen 114 when required. For example, the proximal end of first lumen 112 and/or second lumen 114 may be forked to allow introduction of additional devices as well as a connection to either fluid supply apparatus 140 and/or vacuum source 150. Additionally or alternatively, first lumen 112 and/or second lumen 114 may include side port(s) at or near proximal end 106 for introduction of additional devices.

Figure 2:
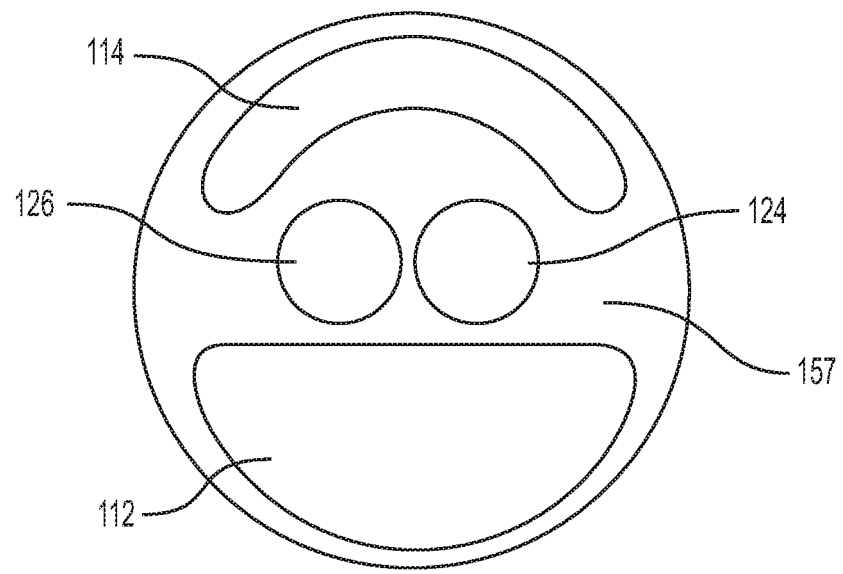
FIG. 2 illustrates an exemplary cross-section of the tube taken at 1-1 of FIG. 1.

FIG. 2 illustrates a cross-sectional view of tube 102 depicting first lumen 112, second lumen 114, imaging device 124, and illumination device 126. This view may, for example, be at line 1-1 of FIG. 1 or proximal end 106 of tube 102. As shown, first lumen 112 may be a semi-circular shaped lumen and second lumen 114 may be an arc- or curved-shaped lumen, but the size and shape of first lumen 112 and/or second lumen 114 are not limited thereto. For example, first lumen 112 and second lumen 114 may have approximately the same cross-sectional shape and size. Either lumen may be configured to supply fluid, apply suction, or both. Lumen 114 may be approximately 0.5 mm to approximately 2.5 mm, approximately 0.5 mm to approximately 2 mm, or approximately 1 mm to approximately 2 mm. Lumen 112 maybe approximately 2 mm in length by approximately 1 mm in breadth, approximately 2.5 mm by approximately 2.5 mm, approximately 2 mm by approximately 1 mm, approximately 3 mm by approximately 2 mm, approximately 2.5 by approximately 1 mm, or approximately 3 mm by approximately 1.5 mm.

FIG. 2 includes imaging device 124 and illumination device 126. These devices may be attached to the distal end 104 of tube 102 using known coupling mechanisms. In some examples, elements 124 and 126 of FIG. 2 may represent lumens for an imaging device and/or an illumination device to be introduced through and/or for necessary fibers/wires/etc. to extend through.

Figure 3:
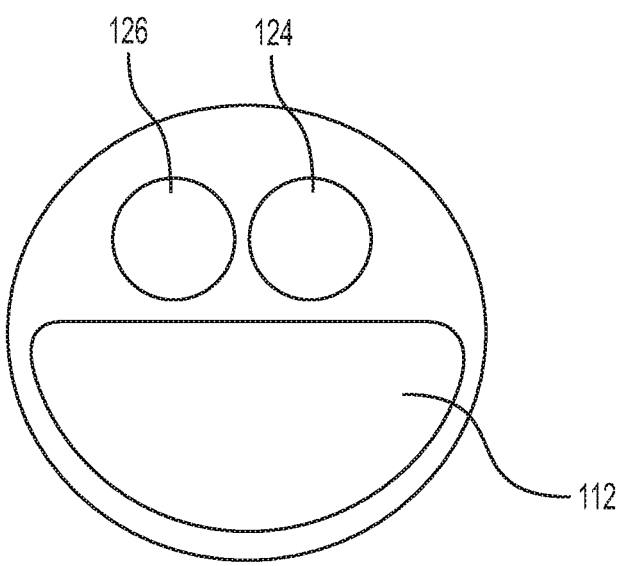
FIG. 3 illustrates an exemplary cross-section of the tube taken at 2-2 of FIG. 1.

FIG. 3 illustrates a cross-sectional view of tube 101 depicting first lumen 112, imaging device 124, and illumination device 126. This view may, for example, be at line 2-2 of FIG. 1 or distal end 104. As shown, second lumen 114 is not present, because, for example, second lumen 114 terminates proximal to the cross-sectional view of FIG. 3, e.g., at suction port 109. As shown, tube 102 may include a generally semi-circular lumen, first lumen 112. It should be noted that first lumen 112 may have any shape or size. In the example illustrated in FIG. 3, first lumen 112 may be configured to provide medical instruments, supply fluid, and/or apply suction.

FIG. 3 includes imaging device 124 and illumination device 126. These devices may be attached to the distal end 104 of tube 102 using known coupling mechanisms. In some examples, elements 124 and 126 of FIG. 3 may represent lumens for an imaging device and/or an illumination device to be introduced through and/or for necessary fibers/wires/etc. to extend through.

C. Insertion and Operation of the Medical Device

Figure 4:
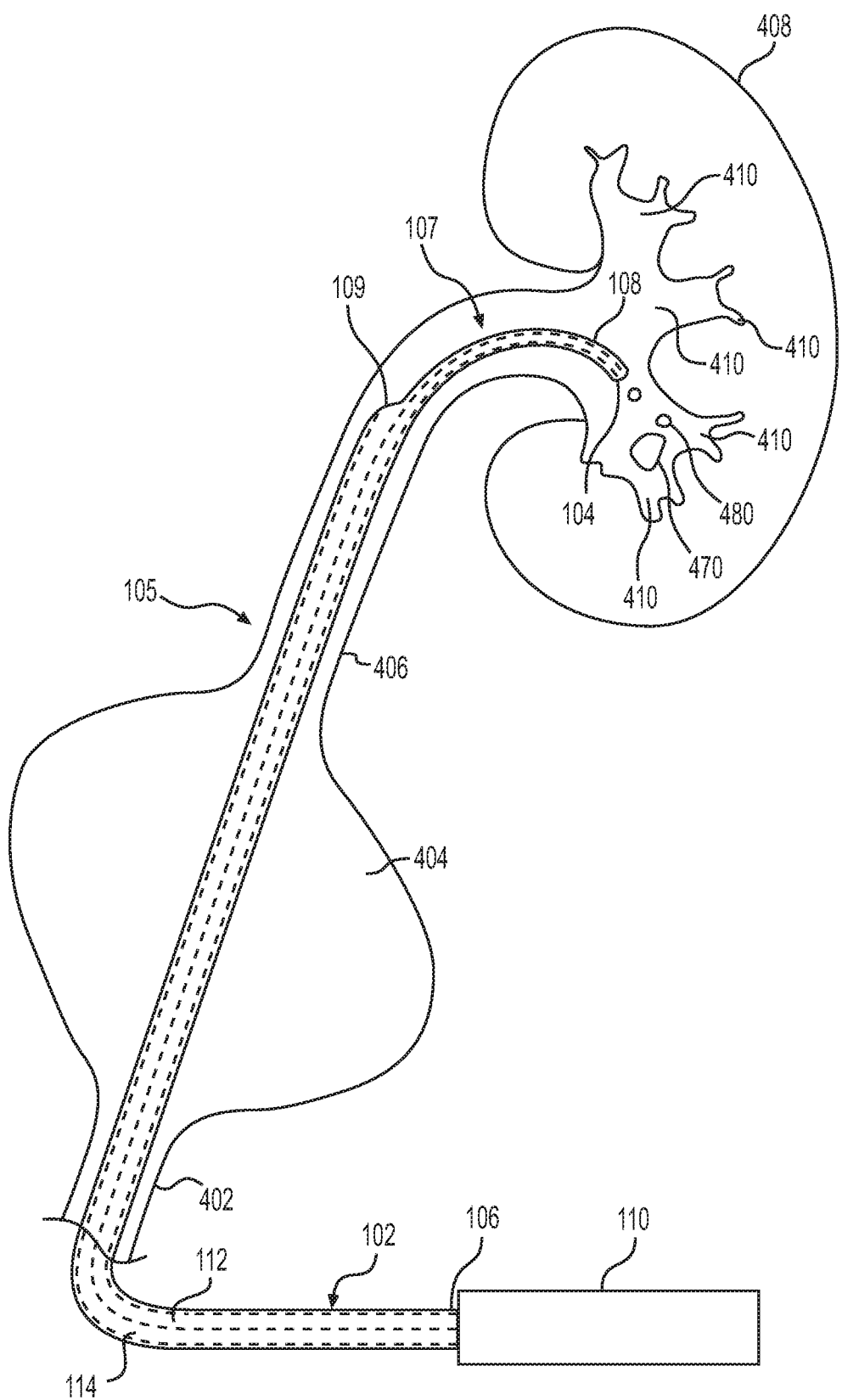
FIG. 4 illustrates an exemplary medical device extending into a patient's body.

Referring to FIG. 4, a patient's urinary tract includes urethra 402, bladder 404, ureter 406, and kidney 408. As shown in FIG. 4, kidney 408 includes calyx 410, including major calyx and minor calyx. In some aspects of the present disclosure, the target area, e.g., the area in which particles, like kidney stones 470 and stone fragments 480, are known or suspected to be located, may be within calyx 410 of the kidney 408. Often, the space within kidney 408 and/or calyx 410 of the kidney 408 is more limited than the space within the ureter 406. Referring to FIG. 4, an operator (e.g., a doctor or other medical professional) may insert distal end 104 of device 100 into the patient's urethra 402. The operator may advance tube 102 so that distal end 104 passes into and through the urinary bladder 404, into and through ureter 406, and into calyx 410 of kidney 408. As there is limited space with calyx 410 of kidney 408, the operator may position first portion 105 of tube 102 and/or suction port 109 in the larger ureter 406. The operator may position a distal opening of first lumen 112 proximate a target area. A target area may be a site where stones and/or stone fragments (e.g., stone 470 and/or stone fragments 480) are known or suspected to be located. An imaging device (e.g., imaging device 124) may be utilized to determine the location of stone(s), as known in the art. The distal end 104 may be adjusted so that first lumen 112 and/or any medical instruments (e.g., laser fiber 120 of FIG. 5) disposed within first lumen 112 may be aimed at the located stone(s). Laser fiber 120 may then be introduced through first lumen 112 to distal end 104.

As shown in FIG. 5, once the laser fiber is in a sufficient position to aim for the kidney stone, the operator may initiate a laser control to break up the kidney stone. FIG. 5 illustrates an enlarged, exemplary distal end 104 of tube 102 in which laser fiber 120 is aimed at kidney stone 470. Laser fiber 120 may be introduced into a patient through first lumen 112. Laser fiber 120 may be connected to and/or controlled by laser control 130. Laser fiber 120 may be utilized to break up kidney stones (e.g., kidney stone 470) into smaller stone fragments (e.g., stone fragments/dust 480).

The operator may connect first lumen 112 to fluid supply assembly 140 and/or may turn on previously connected fluid supply assembly 140 to introduce fluid through first lumen 112 to the target area. The fluid supply assembly 140 may then provide fluid, through first lumen 112, to the distal end 104 of tube 102 and into kidney 408. In some examples, the fluid supplied is a saline solution, for example, 0.9% saline. Fluid supply assembly 140 and laser control 130 may be separately or simultaneously connected to first lumen 112. In addition, first lumen 112 may provide a pathway other instruments (e.g., basket, grasper, etc.).

Before, after, or simultaneously with the operator turning on the fluid supply assembly 140 to introduce fluid through first lumen 112 to the target area, the operator may turn on the suction (e.g., vacuum source 150) to pull the stone fragments/dust 480 into second lumen 114. The arrows in FIG. 5 illustrate an exemplary path of irrigation fluid from first lumen 112 to second lumen 114. In the example illustrated in FIG. 4, suction port 109 is positioned within ureter 406. Thus, if kidney stone 470 is within kidney 408 when it is broken into stone fragments/dust 480, the stone fragments/dust may travel (e.g., naturally or through suction) proximally from the site of treatment into the renal pelvis or into the ureter 406 and then be suctioned into suction port 109 by the suction supplied by vacuum source 150 through second lumen 114. The continuous flow of saline (saline column) along with the stone dust 480 in the ureter may prevent the wall of the ureter from collapsing and being sucked into the suction port 109. Further, in some examples, the use of an automated fluid management device that maintains a constant intrarenal pressure during the procedure will also prevent ureter collapse as insufflation consistency is optimized.

Depending on the size of the patient, the size of the ureter anatomy may vary. In some examples, a portion of the ureter may be enlarged using a balloon dilator at the start of the procedure to ensure that the ureter can accommodate the tube 102. In some examples, suction port 109 may be located in the renal pelvis where there is more room and where irrigant insufflation will work better to maintain expansion of the ureter.

In some example, the fluid may be provided to first lumen 112 at a variety of flow rates. The fluid may be introduced in a continuous flow or pulsed. In some examples, the flow rate may be pulsed at a regular interval, e.g., every few seconds. The pulsed flow may be a flow that is either intermittently interrupted or simply reduced in rate on an intermittent basis. The flow rate may be pulsed at complex flow rate patterns such as periodic and aperiodic oscillatory patterns. A pulsed flow may be created in any way. In one example, the pulse flow may be created by a mechanical pump, e.g., a peristaltic pump. The mechanical pump may apply and release pressure on the fluid at intervals.

The flow rate of the introduced fluid may be balanced with the flow rate caused by the vacuum source. Balanced flow rates can be substantially equal, but need not be exactly equal. A balanced flow rate may be any flow rate that prevents harm to the patient. For example, a balanced flow rate may be any flow rate of the introduction of fluid in relationship to the flow rate of the suction that prevents hydronephrosis and/or prevents the kidney from collapsing due to no fluid in the system, as known in the art. The balanced flow rate may assist in maintaining a pressure equilibrium during operation of the device. In some examples, a pressure sensor may also be located at or near the target area and/or distal end 104 to assist in maintaining a pressure equilibrium.

In addition, the application of suction, e.g., suction through suction port 109, may improve the ability to break kidney stones by creating an anti-retropulsion effect. By applying suction through second lumen 114, a kidney stone may be pulled toward laser fiber 120, thus countering the effect of the laser energy pushing the kidney stone away. This configuration thus assists in generating the smaller stone fragments by pulling the stones into the reach of laser fiber 120. It may also improve the suction of the resulting stone fragments into second lumen 114 and out of the body. For example, by having irrigation from the distal end and suction from a side of tube 102, the inflow fluid is less likely to interfere with the vacuuming of the stone dust. In addition, positioning suction port 109 within the ureter may prevent clogging of suction port 109 and/or second lumen 112. For example, larger stones may not be capable of travelling into the ureter to reach suction port 109, because the entrance to the ureter is partially blocked by second portion 107 of tube 102 and/or there is not sufficient space within the ureter for larger (e.g., not broken up by a laser) stones.

Once the operator determines kidney stone 470 has been broken into sufficiently small fragments 480 (e.g., sufficiently small to pass naturally or to be suctioned into suction port 109) or does not want to continue for other reasons, the laser process may be stopped. Once the stone fragments/dust 480 have been sufficiently removed from the body through suction port 109 and second lumen 114, the operator may cease introduction of irrigational fluid and/or stop suction. In some example, the laser process, introduction of irrigational fluid, and/or application suction may all stop at the same time. In other examples, introduction of irrigational fluid and/or suction may continue after the laser process has stopped.

In some examples, fluid supply assembly 140 and/or vacuum source 150 do not operate at the same time as laser fiber 120. For example, the laser process may cease before introduction of fluid through first lumen 112 and/or application of suction through second lumen 114. In some examples, laser fiber 120 may be removed from first lumen 112 before fluid is introduced through first lumen 112.

At any point, an operator may additionally choose to move the device within the patient. For example, an operator may choose to move distal end 104 of tube 102 to the site of an additional kidney stones. The purpose of repositioning the distal end 104 may be to reach stones or stone fragments that need to be broken into smaller pieces. In some examples, the operator may choose to move tube 102 so that suction port 109 is positioned at a location in which additional stone fragments/dust have accumulated. The purpose of repositioning suction port 109 may be to reach stone fragments/dust that the device was previously unable to suction out. For example, some stone fragments/dust may be positioned proximally to suction port 109 or positioned too distally to be captured by applied suction. An operator may reposition tube 102 any number of times. Once repositioned, any or all of the previously described steps, e.g., the laser process, introduction of fluid, and/or application of suction, may be repeated at the new location.

Once an operator determines no more kidney stones can and/or should be broken apart and/or no more stone fragments/dust can and/or should be removed, the ureteroscope (e.g., tube 102) may be removed from the patient's body.

The many features of the disclosure are apparent from the detailed specification, and thus, it is intended by the appended claims to cover all such features of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A medical device, comprising:
a tube having a distal end, a proximal end, a port located proximal of the distal end, and a length of the tube extending between the proximal end and the distal end, wherein a first portion of the tube is proximal of the port and has a first cross-sectional area and a second portion of the tube is distal of the port and has a second cross-sectional area smaller than the first cross-sectional area;

a first lumen extending from the proximal end to the distal end of the tube and having a distal opening on a distalmost face of the distal end of the tube;

a second lumen in communication with the port and fluidly connecting the proximal end of the tube with the port; and a laser fiber disposed within the first lumen, the laser fiber configured to extend distally from the distalmost face of the distal end of the tube through the distal opening, wherein the first cross-sectional area includes a cross-section of only one additional lumen than the second cross-sectional area, wherein the first portion of the tube defines an outermost wall of each of the first lumen and the second lumen, and wherein a position of the first lumen is fixed relative to a position of the second lumen.

2. The medical device of claim 1, wherein the port is distal to the proximal end by a distance of approximately half to approximately three-quarters the length of the tube.

3. The medical device of claim 2, wherein the port is located approximately 5 cm to approximately 15 cm from the distal end.

4. The medical device of claim 3, wherein the second lumen terminates at the port.

5. The medical device of claim 1, further comprising:
a fluid supply assembly connected to the first lumen.

6. The medical device of claim 5, wherein the laser fiber is coupled to a laser control at a same time the fluid supply assembly is connected to the first lumen, and a fluid is configured to be expelled from the first lumen simultaneously with an operation of the laser fiber via the laser control.

7. The medical device of claim 5, further comprising:
a vacuum source connected to the second lumen.

8. The medical device of claim 1, wherein the port is angled relative to a longitudinal axis of the second lumen.

9. The medical device of claim 1, further comprising:
an illumination device extending through the tube.

10. The medical device of claim 9, further comprising:
an imaging device extending through the tube.

11. The medical device of claim 1, wherein the first cross-sectional area is approximately 3 mm to approximately 5 mm.

12. The medical device of claim 11, wherein the second cross-sectional area is approximately 2 mm to approximately 5 mm.

13. The medical device of claim 1, wherein the port is substantially crescent-shaped.

14. The medical device of claim 1, wherein the distalmost face of the distal end of the tube is a planar distalmost face.

15. A medical device, comprising:
a tube having a distal end, a proximal end, and a port located proximal of the distal end;
a first lumen having a proximal opening at a proximal end and only one distal opening at a distal end, wherein the only one distal opening is located on a distalmost face of the distal end of the tube, and the first lumen is in communication with the distal end of the tube and fluidly connects the distal end of the tube with a fluid supply assembly through the only one distal opening;
a second lumen in communication with the port and fluidly connecting a vacuum source with the port; and
an imaging unit disposed on the distalmost face of the distal end of the tube and extending within the tube from the distal end to the proximal end of the tube, wherein the imaging unit is positioned between the first lumen and the second lumen in a cross-sectional plane of the tube perpendicular to a longitudinal axis of the tube from the port to the proximal end of the tube,
wherein the port is tapered such that a proximalmost portion of a wall defining the port is a radially outermost surface of the wall and a distalmost portion of the wall is a radially innermost portion of the wall, and
wherein the tube extends along a fixed distance between the port and the distalmost face of the distal end of the tube.

16. The medical device of claim 15, wherein the port is at least partially distal-facing.

17. The medical device of claim 15, wherein the imaging unit comprises:
an imaging device disposed on the distalmost face of the distal end of the tube; and
a lighting device disposed on the distalmost face of the distal end of the tube.

18. The medical device of claim 15, wherein the imaging unit extends from the distal end to the proximal end of the tube within a wall of the tube, and the wall of the tube separates the first lumen and the second lumen within the tube from the port to the proximal end of the tube.

19. A medical device, comprising:
a laser fiber; and
a tube having a distal end and a proximal end, the tube including:
a first lumen extending through an entirety of the tube from the proximal end of the tube to the distal end of the tube, wherein the first lumen includes a fluid port for supplying a fluid from the first lumen during an operation of the medical device, and wherein the laser fiber extends distally from the first lumen through a distal opening of the first lumen on a distalmost face of the distal end of the tube during the operation of the medical device; and
a second lumen independent of the first lumen, wherein the second lumen extends through a portion of the tube from the proximal end of the tube to a suction port proximal to the distal end of the tube, wherein the tube extends along a fixed distance between the suction port and the distalmost face of the distal end of the tube, wherein the fixed distance is in a range of approximately 5 cm to approximately 15 cm, and wherein the suction port creates a suction during the operation of the medical device,
wherein the portion of the tube defines an outermost wall of each of the first lumen and the second lumen, and
wherein a position of the first lumen is fixed relative to a position of the second lumen.

20. The medical device of claim 19, wherein the fluid is configured to be expelled from the first lumen simultaneously with an operation of the laser fiber and the suction created by the suction port.

* * * * *